US00PP08778P

United States Patent [19]

Meilland

[11] Patent Number: Plant 8,778

[45] Date of Patent: Jun. 14, 1994

[54] FLORIBUNDA ROSE PLANT NAMED 'MEISPREYO'

[75] Inventor: Alain A. Meilland, Antibes, France

[73] Assignee: The Conard-Pyle Company, West Grove, Pa.

[21] Appl. No.: 63,554

[22] Filed: May 11, 1993

[51] Int. Cl.[5] ..... A01H 5/00

[52] U.S. Cl. ..... Plt./24

[58] Field of Search ..... Plt. 15, 24

*Primary Examiner*—Howard J. Locker

*Attorney, Agent, or Firm*—Burns, Doane, Swecker & Mathis

[57] ABSTRACT

A new and distinct variety of Floribunda rose plant is provided which abundantly forms attractive semi-double blossoms commonly in the form of clusters which are long lasting when cut and placed in a vase. The blossoms are a very stable Lemon Yellow in coloration. The plant exhibits vigorous vegetation and is semi-erect. The new variety is well adapted for greenhouse forcing and is particularly well suited for cut flower production. Good resistance to cryptogamic diseases also is exhibited.

1 Drawing Sheet

SUMMARY OF THE INVENTION

The new variety of Floribunda rose plant was created by artificial pollination wherein two parents were crossed which previously had been studied in the hope that they would contribute the desired characteristics. The female parent (i.e., the seed parent) of the new variety was the Meidonbour variety (non-patented in the United States). The male parent (i.e., the pollen parent) of the new vareity was the Meijaudiair variety (non-parented in the United States). The parentage of the new variety can be summarized as follows:

Meidonbour × Meijaudiair.

The seeds resulting from the above pollination were sown and 7 small plants were obtained which were physically and biologically different from each other. Selective study resulted in the identification of a single plant of the new variety.

It was found that the new variety of Floribunda rose plant of the present invention possesses the following combination of characteristics:

(a) forms in abundance attractive semi-double blossoms commonly borne in clusters which are Lemon Yellow in coloration and are long lasting when cut and placed in a vase,
(b) exhibits a semi-erect growth habit,
(c) forms medium green adult wood,
(d) forms vigorous vegetation,
(e) is particularly well suited for cut flower production, and
(f) is not particularly affected by cryptogamic diseases.

The flower coloration has been found to be very stable. Also, the plant is well adapted for greenhouse forcing.

The new variety undergoes asexual propagation by a number of routes, including budding, grafting, cuttage, etc. The characteristics of the new variety have been found to be strictly transmissible by such asexual propagation from one generation to another in both France and the United States.

The new variety has been named the Meispreyo variety.

BRIEF DESCRIPTION OF PHOTOGRAPH

The accompanying photograph shows as nearly true as it is reasonably possible to make the same, in a color illustration of this character, typical specimens of the plant parts of the new variety. The rose plants of the new variety were two years of age and were observed during February while budded on *Rosa indica* understock and growing in greenhouses at Cap d' Antibes, France.

DETAILED DESCRIPTION

Figures 1, 2, 3, 4, 5, 6, 7, 8, 9, 10, 11, 12, 13, 14, 15:
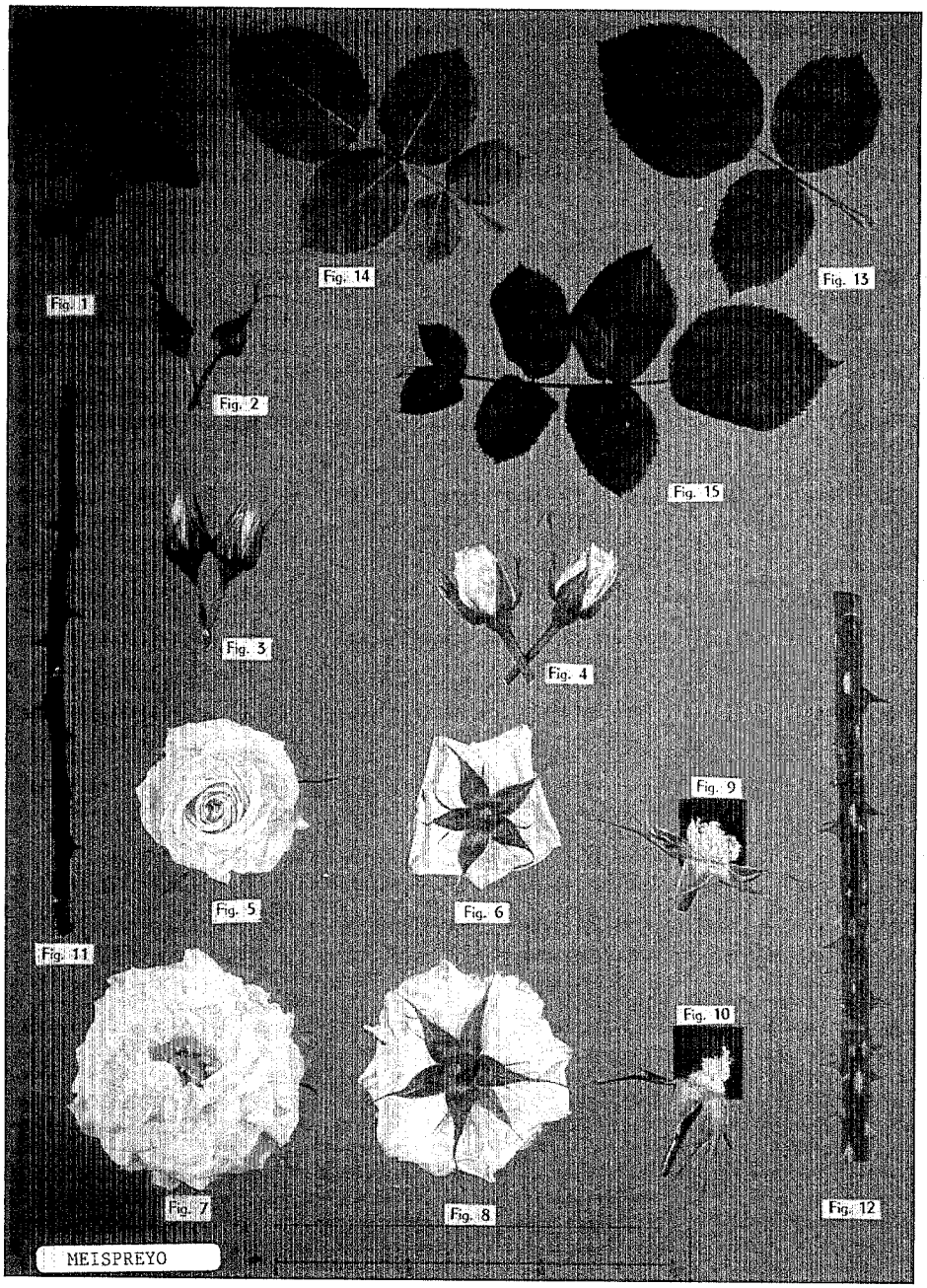
FIG. 1 illustrates a specimen of a young shoot.
FIG. 2 illustrates a specimen of a pair of floral buds before the opening of the sepals.
FIG. 3 illustrates a specimen of a pair of floral buds at the opening of the sepals.
FIG. 4 illustrates a specimen of a pair of floral buds at the opening of the petals.
FIG. 5 illustrates a specimen of an open flower — plan view — obverse.
FIG. 6 illustrates a specimen of an open flower — plan view — reverse.
FIG. 7 illustrates a specimen of a fully open flower — plan view — obverse.
FIG. 8 illustrates a specimen of a fully open flower — plan view — reverse.
FIG. 9 illustrates a specimen of a floral receptacle showing the arrangement of the stamens and pistils.
FIG. 10 illustrates a specimen of a floral receptacle showing the arrangement of the pistils (stamens removed)
FIG. 11 illustrates a specimen of a flowering stem.
FIG. 12 illustrates a specimen of an adult main branch.
FIG. 13 illustrates a specimen of a leaf with three leaflets — upper surface.
FIG. 14 illustrates a specimen of a leaf with five leaflets — under surface.
FIG. 15 illustrates a specimen of a leaf with seven leaflets — upper surface.

The chart used in the identification of the colors is that of The Royal Horticultural Society (R.H.S. Colour Chart). The terminology which precedes reference to the chart has been added to indicate the corresponding color in more common terms. The description is based on two year old specimens of the new variety during February while budded on *Rosa indica* understock and growing in greenhouses at Cap d' Antibes, France.

Class: Floribunda.

Plant:

*Height.*—When the plants are cut to a height of 85 cm., the flowering stems commonly measure approximately 30 to 50 cm. When grown in fields at Wasco, Calif., the plants commonly achieve a height of approximately 70 cm. at the end of one growing season.

*Habit.*—Semi-erect.

Branches:

*Color.*—Young stems: medium green, Greeen Group 143A. Adult wood: medium green, Green Group 137C.

*Thorns.*—Size: small. Quantity: average. Color: pinkish on young stems, and greenish-pink on mature wood.

Leaves:

*Stipules.*—Adnate, pectinate, narrow and linear.

*Petioles.*—Upper surface: striped reddish-brown on young foliage and medium green on mature wood with more or less glandular edges. Under surface: light green, with numerous prickles.

*Leaflets.*—Number: 3, 5 (most often), and 7. Shape: oval to rounded. Serration: single and regular. Texture: consistent. General appearance: dense, semi-matte foliage. Color (young foliage): Upper surface: dark green, Green Group 137A. under surface: grayish green, Greyed-Green Group 191A. Color (adult foliage): Upper surface: dark green, Green Group 137A. Under surface: grayish green, Greyed-Green Group 191A.

Inflorescence:

*Number of flowers.*—Commonly in clusters of up to 12 blooms.

*Peduncle.*—Medium green, covered with small prickles and glandular acicules, and approximately 5 to 6 cm. in length on average.

*Sepals.*—Upper surface: tomentose and greenish in coloration. Under surface: medium green, smooth, and the outer sepals commonly possess glandular edges and commonly are widely appendiculated.

*Buds.*—Shape: conical. Length: approximately 2 2.5 cm. on average. Size: average. Color upon opening: Upper surface: Lemon Yellow, Yellow Group 13A, sometimes slightly edged with Jasper Red, Red Group 39C. Under surface: Lemon Yellow, Yellow Group 13A, sometimes slightly edged with Jasper Red, Red Group 39C.

Flower.—Shape: as a shallow cup, semi-double. Diameter: approximately 6 cm. on average. Color (when opening begins): Upper surface: Lemon Yellow, Yellow Group 13A. under surface: Lemon Yellow, Yellow Group 13A. Color (when blooming): Upper surface: Lemon Yellow, Yellow Group 13A, sometimes turning lighter yellow near the edge. Under surface: Lemon Yellow, Yellow Group 13A, sometimes turning lighter yellow near the edge. Color (at end of opening): Upper surface: Lemon Yellow, Yellow Group 13A, sometimes turning lighter yellow near the edge. Under surface: Lemon Yellow, Yellow Group 13A, sometimes turning lighter yellow near the edge. Fragrance: none. Lasting quality: long lasting blossoms when cut and placed in a vase. Petal drop: good. Petal number: approximately 19 to 20 on average. Petal texture: consistent. Stamen number: approximately 168 on average. Anthers: normal, ochre in coloration, located below the stigmas. Filaments: bright yellow and irregular in height. Pistils: approximately 111 on average. Stigmas: greenish to straw-like. Styles: greenish straw-colored, and irregular in height. Receptacle: light green, and in longitudinal section in the shape of a wide funnel at the dehiscence of the anthers.

Development:

*Vegetation.*—Very vigorous.

*Blooming.*—Abundant.

*Resistance to diseases.*—Good.

*Aptitude to be forced.*—Good.

I claim:

1. A new and distinct variety of Floribunda rose plant characterized by the following combination of characteristics:

(a) forms in abundance attractive semi-double blossoms commonly borne in clusters which are Lemon Yellow in coloration and are long lasting when cut and placed in a vase, (b) exhibits a semi-erect growth habit, (c) forms medium green adult wood, (d) forms vigorous vegetation, (e) is particularly well suited for cut flower production, and (f) is not particularly affected by cryptogamic diseases;

substantially as herein shown and described.

* * * * *

MEISPREYO